(12) United States Patent
Connolly et al.

(10) Patent No.: US 7,910,127 B2
(45) Date of Patent: Mar. 22, 2011

(54) USE OF LACTIC ACID BACTERIA FOR IMPROVING FOOD LYSINE ABSORPTION OF PET ANIMALS

(75) Inventors: Eamonn Connolly, Lidingö (SE); Bo Mollstam, Lerum (SE)

(73) Assignee: Biogaia AB, Stockholm (SE)

( * ) Notice: Subject to any disclaimer, the term of this patent is extended or adjusted under 35 U.S.C. 154(b) by 242 days.

(21) Appl. No.: 12/072,415

(22) Filed: Feb. 26, 2008

(65) Prior Publication Data
US 2008/0213431 A1    Sep. 4, 2008

Related U.S. Application Data

(60) Provisional application No. 60/904,679, filed on Mar. 2, 2007.

(51) Int. Cl.
*A23K 1/165* (2006.01)
*A01N 63/00* (2006.01)

(52) U.S. Cl. .................. 424/442; 424/234.1; 424/93.45; 435/252.9

(58) Field of Classification Search .................. None
See application file for complete search history.

(56) References Cited

U.S. PATENT DOCUMENTS

2003/0082277 A1 * 5/2003 Sokhey et al. .................. 426/92
2003/0152664 A1   8/2003 Couzy et al.
2003/0190309 A1 * 10/2003 Zink et al. .................. 424/93.45

FOREIGN PATENT DOCUMENTS
WO    WO9856263 A1    12/1998

OTHER PUBLICATIONS

Valeur et al (Applied and Environmental Microbiology, 70(2):1176-1181, Feb. 2004).*
Ahlstrom, O et al., Comparative nutrient digestibility in dogs, blue foxes, mink and rats, J. Nutr. 128:2676S-2677S, 1998.
Boisen, S. et al., Ideal amino acid profiles as a basis for feed protein evaluation, Livestock Production Sci. 64:239-251, 2000.
Dahlman, T. et al., Influence of protein level and supplementary L-methionine and lysine on growth performance an . . . , Acta Agric. Scand., Sect. A, Animal Sci. 52:174-182, 2002.
Dahlman, T., Protein and amino acids in the nutrition o the growing-furring blue fox, U. of Helsinki, Dept. of Animal Science, Publications, 2003.
Glem-Hansen, N., Utilization of L-cystine and L- and D-methionine by mink during the period of intensive hair growth, Acta Agriculture Scand. 32L167-170, 1982.
Kerminen-Hakkio, M. et al., Effect of dietary protein level and quality on growth rate and fur parameters . . . , Proc. VII Internat. Sci. Cong. in Fur Animal Prod. 24:7-12, 2000.
Montes, A. et al., The use of probiotics in food-animal practice, Vet. Med. , Mar. 1993.
Roth, F. et al., The ideal dietary amino acid pattern for broiler-chicks of age 7 to 28 days, Arch. Geflugelk 65:199-206, 2001.
Thwaites, D. et al., Na+-independent lysine transport in human intestinal Caco-2 cells, J. Membrane Biol. 151:215-224, 1996.

* cited by examiner

*Primary Examiner* — Patricia A Duffy
(74) *Attorney, Agent, or Firm* — Lynn E. Barber

(57) ABSTRACT

This invention relates to the selection and use of nonpathogenic, lysine-uptake stimulating lactic acid bacteria strains, and products and methods using such strains for example for improvement of fur-coat and claws quality in pet-animals.

9 Claims, 1 Drawing Sheet

USE OF LACTIC ACID BACTERIA FOR IMPROVING FOOD LYSINE ABSORPTION OF PET ANIMALS

CROSS-REFERENCE TO RELATED APPLICATIONS

This application claims priority from U.S. provisional application Ser. No. 60/904,679 filed Mar. 2, 2007.

BACKGROUND OF THE INVENTION

1. Field of the Invention

This invention relates to the selection and use of nonpathogenic, lysine-uptake stimulating lactic acid bacteria strains, and products and methods using such strains for example for the improvement of fur and claw quality in pet-animals.

2. Description of the Related Art

In 1908, the Russian biologist Eli Metchnikoff credited the long lives of certain Bulgarian and Russian citizens to the consumption of large amounts of fermented milk products (1). The key organism in these foods was later identified as *Lactobacillus acidophilus*, a lactic acid-producing bacteria (2). The lactic acid-producing bacteria are so named for their ability to produce lactate. However, lactate production is only one of many benefits derived from this collection of bacteria.

Based on the work of Metchnikoff and others, scientists developed the idea of probiotic microorganisms, directly feeding live, lactic acid-producing bacteria and yeast to animals for improving their health and performance. The observed benefits may result from: 1) competition for attachment sites in the digestive tract, 2) competition for essential nutrients, 3) production of anti-microbial substances, 4) increasing the growth of beneficial bacteria and 5) stimulating the immune system (3).

Some disease-causing bacteria reduce an animal's ability to absorb nutrients by disrupting the lining of the small intestine (4). Studies indicate that the lactic acid-producing bacteria attach to the small intestine and produce substances to prevent disease-causing organisms from binding to the intestinal wall (5). In addition, the attachment of the beneficial bacteria may increase the absorptive surface area of the small intestine and enhance enzyme activity for greater nutrient absorption by the animal (8,6).

Bacteria, both health-promoting and disease-causing, require certain nutrients for growth. Lactic acid-producing bacteria could utilize vitamins, amino acids or other nutrients that might otherwise support the growth of harmful bacteria (7).

Considerable research has focused on the ability of direct-fed microbial cultures to produce substances that inhibit disease-causing organisms. Lactic, acetic and formic acid lower the intestinal pH to create an environment unsuitable for harmful organisms (4). Lactic acid-producing bacteria also secrete hydrogen peroxide, resulting in conditions unfavorable for oxygen-requiring microorganisms (8).

Two groups of antimicrobial substances have been identified, low molecular weight antimicrobial substances, for example, reuterin, produced by *L. reuteri;* and bacteriocins. Bacteriocins are microbially produced substances that inhibit the growth of bacteria that are often genetically related (4). Bacteriocins are polypeptides and their inhibitory properties are destroyed by proteases while Reuterin, a broad-spectrum antimicrobial substance, is not a polypeptide and its antimicrobial activity is unaffected by proteases.

Research has documented the ability of lactic acid-producing bacteria to inhibit *E. coli, Salmonella typhimurium, Staphylococcus aureus* and *Clostridium perfingens* (7). The reduction of diarrhea-causing organisms is especially important in newborn and young animals.

There are however few studies done on probiotics in companion animals. One recent study (9) investigated the application of *Lactobacillus acidophilus* DSM 13241 in canines. This strain was chosen on the basis of its growth characteristics, antimicrobial activity toward pathogens, and survival rate in gut models. Feeding of healthy dogs resulted in a significant increase in the population of recoverable lactobacilli in the feces with a concomitant decrease in the clostridia population. The researchers concluded that feeding of the probiotic resulted in positive changes in the gut microbiology and in systemic effects that suggested immune system stimulation as observed in humans after they consumed *Lactobacillus* spp. (10).

Like dogs, cats, mink (*Mustela vison*) and blue foxes (*Alopex lagopus*) belong to the mammalian order Carnivora. The carnivores are adapted to relatively concentrated and highly digestible diets, and are characterized by a gastric stomach and a relatively short and uncomplicated intestine. The mink lacks a cecum and has a short digestive tract with very limited bacterial activity in the colon. Dogs and foxes have little cecal capacity and an unsacculated colon, but some bacterial fermentation takes place in the cecum and colon (11).

Protein is vital for growth, repair, and maintenance of body tissue. It forms the basis of enzymes and antibodies. For animals and birds, a lot of protein is used as energy to make fur, feathers and claws, which are primarily alpha-keratin. Alpha-keratins consists of long alpha-helical polypeptides, which are wound around each other to form triple helixes. For fur animals in general, sulfur-containing amino acids are usually considered to be the first limiting ones ((12). Protein to make fur, feathers and claws has to come from the diet. The diets must supply enough amino acids to meet requirements of the essential amino acids with enough excess amino acids to supply nitrogen that makes the nonessential amino acids. Additional protein in the diet cannot be stored and will be converted to fat or excreted by the kidneys.

Lysine is an essential amino acid and thus unable to be synthesized by transamination. It helps make fat usable to the body by producing carnitine, removes toxins from the body, builds fur, feathers and bone. High levels increase the need for arginine. Lysine is highly unstable in intact protein. It reacts with glucose and the reaction accelerates in the presence of warmth and moisture. Research on young pigs and poultry has found lysine to be the first limiting amino acid for growth (e.g. Boisen et al., 2000; (13,14).

Methionine and cysteine are nutrient amino acids, and the most active of the essential amino acids. They are used to make such important molecules as carnitine (used in the transport of fatty acids), creatine, niacin, polyamines, and purines (used to create uric acid). They are also used in the making of fur and feathers. Cysteine can be synthesized from methionine, and therefore it is classified as non essential. However, cysteine and its oxidation product cystine can satisfy approximately 50 percent of the need for total sulfur amino acids and in this way can reduce the need for methionine. Methionine can not be synthesized from cysteine, and therefore it is essential. Methionine can meet the total need for sulfur amino acids in the absence of cystine. Some studies have found methionine to be the first limiting amino acid for hair growth and fur quality in mink. (15,16,17,18,19,20,21)

In most household pets, a healthy skin and coat indicates an animal in general good health. Since skin and coat problems are common in household pets, much research has gone into providing diets which repair deteriorations in skin and coat conditions, thus providing a basic level of healthy skin and coat as described hereinafter.

Research shows that supplementation of a complete and balanced commercial dog food with zinc plus linoleic acid can make significant and substantial enhancements of the skin and coat conditions in dogs. The dogs showed significant improvement in coat gloss and coat scale when compared to control groups receiving a standard diet. This approach is also described in patent EP0987961B1.

Nutrition may impact skin barrier function. The international patent application WO0207531A1 discloses the use of dietary lipids containing anti-microbial fatty acids for the preparation of a food composition intended for improving or maintaining the skin health and/or coat quality.

In the study by Kerminen-Hakkio (21) poor protein quality in mink reduced pelt length on an average by 4 cm. Best overall fur quality was observed in the good quality, high level protein group. The authors conclude that deficiencies in the supply of indispensable amino acids cannot be totally compensated for by increasing the level of protein in the diet.

In some cases, the non-essential amino acids should still be supplemented to ensure optimal available quantity. We have found that available methionine should be balanced with lysine also in food for cats and dogs to improve fur and claw growth and quality. A complimentary way of making better use of lysine from the food, rather than just feeding more, is to look for ways to improve it's absorption.

It is known that animal feeding with Lactic acid bacteria (LAB) is growth-promoting due to generally improved absorption of nutrients. In today's modern animal breeding, a lot of countries already use feed additives which contain probiotic microorganisms for fattening animals. When an animal consumes LAB, they colonize its digestive tract and start to produce enzymes that digest starch (amilase), proteins (proteinases), fat (lipases). These enzymes contribute to the disintegration of complex organic compounds in fodder into low-molecular compounds. The animals can make better use of these low-molecular compounds. Their appetite improves, the fodder conversion rate gets better and the production performances are improved. The use of LAB in animal feeding also contributes to immune defenses against pathogens. LAB disintegrate carbohydrates into lactic acid which reduces pH of the digestive tract content, which become an extremely unfavorable surrounding for pathogen microorganisms.

We have surprisingly found that different strains of LAB present in the food or in the GI-tract can differently aid in the absorption of amino acids, specifically lysine. And that such difference can be measured, thereby making it possible to select the specific strains of lactic acid bacteria that will improve the lysine uptake the most.

The Caco-2 cell system has proved a suitable model system for intestinal epithelial permeability studies (22) of both nutrients, [peptides and amino acids (23,24,25,26)] and pharmaceutical products (27,24) A study performed by Twaites 1996 described the ability of intestinal Caco-2 cells to transport the dibasic amino acid lysine (28).

However there have been few studies on *Lactobacillus* facilitating or increasing the absorption of amino acids from the diet in pet animals.

Bacterial protein meal (BPM) produced by continuous bacterial fermentation using a defined mixture of four different bacteria (*Methylococcus capsulatus, Alcaligenes acidovorans, Bacillus brevis* and *Bacillus firmus*) and natural gas as the carbon and energy source is a novel high-protein feed ingredient. A study was conducted to extend the knowledge of BPM as an ingredient of diets for dogs, using the blue fox as a model animal. The animals revealed generally good growth but there were no data present of fur quality improvement (7).

Patent WO 01/17365A1 describes a method for improving and maintaining the skin and coat system of a pet where the nutritional agent may be a prebiotic or any probiotic microorganism. The applicants mention seventeen different bacterial genera as probiotics and almost thirty specific examples of probiotic microorganisms. *Bacillus coagulans* Lacris-S strain (SANKYO LIFETECH CO., LTD, Hongo, Bunkyo-ku, Tokyo, Japan) is the only specific strain described and there is no selection of preferred strains mentioned, and nor any based on LAB strains' ability to stimulate lysine uptake.

Although the use of probiotics for better fur and feathering in animals is known in the art, it was not previously known that different probiotic strains varies in their ability to improve the quality of the fur and claws of an animal, for example a dog or a cat, and that this ability is correlated with a probiotic strain's influence on lysine absorption in the gut of the animal.

It is therefore an object of the present invention to select such more suitable strains by analyzing their ability to directly facilitate or improve the absorption of lysine in the animal and to use such a selected strain in animal feed or supplement for example to improving fur and claw quality of a dog or a cat. A new strain *Lactobacillus reuteri*, ATCC PTA-6127, is shown to stimulate lysine-uptake in fur-animals and this property results in improved fur and claw quality.

Other objects and advantages will be more fully apparent from the following disclosure and appended claims.

SUMMARY OF THE INVENTION

This invention relates to the selection and use of nonpathogenic, lysine-uptake stimulating lactic acid bacteria strains, and products and methods using such strains for treatment and prophylaxis of fur and claw quality in pet-animals.

DETAILED DESCRIPTION OF THE INVENTION AND PREFERRED EMBODIMENTS THEREOF

Figure 1:
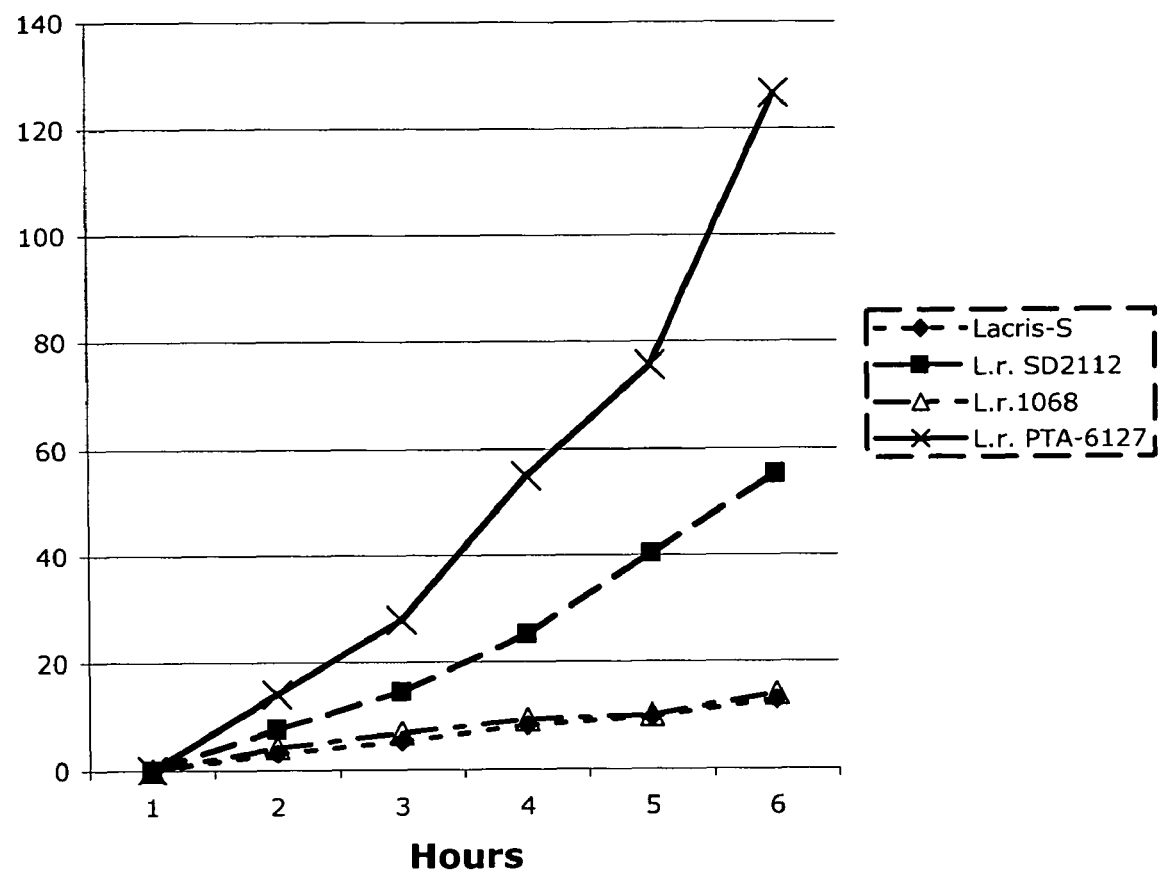
FIG. 1 The bar graph shows the influence of $7.0 \times 10^7$ cfu/ml different LAB strains of on the uptake of lysine by Caco-2 intestinal cells. Strains used are *Lactobacillus reuteri* ATCC PTA-6127, *Lactobacillus reuteri* 1068, *Lactobacillus reuteri* SD2112 and *Bacillus coagulans* Lacris-S strain.

This invention relates to the selection and use of nonpathogenic, lysine-uptake stimulating lactic acid bacteria strains, and products and methods using such strains for treatment and prophylaxis of fur and claw quality in pets.

It is one object of the present invention to select best suitable strains by analyzing their ability to directly facilitate or improve the absorption of lysine in the animal and to use such a selected strain in animal feed or supplement for example to improving fur and claw quality of a dog or a cat. A new strain of *Lactobacillus reuteri* (ATCC PTA-6127) is shown to stimulate lysine-uptake in fur-animals and this property results in improved fur and claw quality. This strain was deposited at the American Type Culture Collection (Manassas, Va.) under the Budapest Treaty on Jul. 22, 2004. All restrictions upon availability to the public will be irrevocably removed upon granting of the patent.

The product of the invention may be in forms such as feed, or a tablet or a capsule or other formulations and standard methods of preparing the underlying product as are known in the art, including the selected LAB culture. Thus, the product containing this feed mixture may be in the form selected from the group consisting of feed, tablets, and capsules.

While certain representative embodiments have been set forth herein, those skilled in the art will readily appreciate that modifications can be made without departing from the spirit or scope of the invention.

EXAMPLE 1

Preparation of Cell Culture

Caco-2 cells (ATCC Number: HTB-37, Manassas, Va., USA) were cultured as described in (Thwaites et al., 1993a; 1993b). Cell monolayers were prepared by seeding at high density ($4.4$-$5.0°$-$10^5$ cells/cm$^2$) onto 12 or 24.5 mm diameter tissue culture inserts [Transwell polycarbonate filters (Costar)]. Cell monolayers were maintained at 37° C. in a humidified atmosphere of 5% $CO_2$ in air. Cell confluence was estimated by microscopy and determination of transepithelial resistance. Radiolabeled fluxes for lysine were performed 18-25 days after seeding and 18-24 hr after feeding.

EXAMPLE 2

Method for Selecting *L. Reuteri* Strains for Intestinal Lysine Uptake

Caco-2 cells monolayers were washed (4 times in 500 ml of modified Krebs buffer (of composition (all mmol/l), NaCl 140, KCl 5.4 CaCl$_2$ 2.8, MgSO$_4$ 1.2, NaH$_2$PO$_4$ 0.3, KH$_2$PO$_4$ 0.3, HEPES 10, glucose 10 (pH to 7.4 at 37° C. with Tris base))) or Na+-free Krebs buffer where appropriate (as above but choline Cl$^-$ replacing NaCl and NaH$_2$PO$_4$ and placed in 6-wells plates (Life Technologies) containing 2 ml of prewarmed (37° C.) Na+-free Krebbs buffer. Aliquots of fresh Krebs buffer or Na+-free Krebbs buffer were placed in the chamber. Radiolabeled lysine ((3H) Amersham) was used at tracer concentrations (0.2 microCi/ml). Epithelial layers were then incubated with various LAB to be tested; *Lactobacillus reuteri* ATCC PTA-6127, *Lactobacillus reuteri* 1068, *Lactobacillus reuteri* SD2112 and *Bacillus coagulans* Lacris-S strain at the concentration of $7.0 \times 10^7$ cfu/ml for 6 hours at 37° C. 200 microL samples were taken every 60 minutes from basal solution for determination of transepithelial transport. The radiolabel was determined by scintillation counting. For results see FIG. 1.

EXAMPLE 3

Manufacturing of Feed Products Containing Selected Strain

In this example, *L. reuteri* "Shiny" (ATCC PTA-6127) is selected based on good growth characteristics in general and favorable results in the earlier mentioned selection in Example 2 in order to add the strain to a commercial product. The *L. reuteri* Shiny strain is grown and lyophilized, using standard methods for growing *Lactobacillus* in the industry.

A feed mixture is made up of corn, corn gluten, chicken and fish meal, salts, vitamins and minerals. The feed mixture is fed into a preconditioner and moistened. The moistened feed leaving the preconditioner is then fed into an extruder-cooker and gelatinized. The gelatinized matrix leaving the extruder is forced through a die and extruded. The extrudate leaving the die head is cut into pieces suitable for feeding to dogs, dried at about 140° C. for about 20 minutes, and cooled to form pellets. The water activity of the pellets is about 0.6.

The pellets are sprayed with a coating substrate comprising tallow fat. The probiotic, *L. reuteri* "Shiny" (ATCC PTA-6127), is applied by dry spraying at a level of $10^7$ CFU/gram of product, before the tallow sets so as to adhere to or be partially penetrated in the fat layer. Results from storage at 37° C. for 8 weeks indicate that the micro-organisms display excellent stability and are likely to be stable after one year of storage at normal conditions.

EXAMPLE 4

Dog Trial

A trial is conducted using 45 Beagle-dogs. The dogs are fed a standard dried diet corresponding to diet in example 3 for a week before the beginning of the trial. Immediately prior to the beginning of the trial, the coat condition of the participating dogs is assessed by an evaluation panel as described in Example 5. The dogs are separated into three groups of 15 dogs. One group of dogs is fed the dried pellets coated with *L. reuteri* "Shiny" (ATCC PTA-6127), the other group of dogs is fed the dried pellets coated with *L. reuteri* strain 1068 and the third group continues to the standard diet, thus providing a control diet. All groups are given free access to the food and to water. After 12 weeks, the coat condition of each dog is again evaluated. The dogs which are fed the pellets with *L. reuteri* "Shiny" coating have a significantly shinier appearance and display no noticeable dandruff than the dogs on fed on pellets with the *L. reuteri* 1068 strain and the dogs in the control group.

EXAMPLE 5

Growth of Claw and Fur Characteristics

The dogs claws in Example 4 are both scored by a skilled nail groomer and the fur by two experienced dog show judges, specializing in the Beagle breed. Before the trial the dogs are evenly distributed between the groups by fur and claw quality. After 12 weeks the nails are evaluated for quality against splitting when cut and growth and scored on a five level scale with 1 being poor and 5 being excellent. The fur is evaluated for overall quality, dandruff, fur length and shine on a scale ranging from 1 (poorest) to 5 (best).

| Treatment | L.r PTA-6127 | L.r 1068 | Control |
|---|---|---|---|
| Average score: Fur after 12 w. | 4.8 | 3.1 | 2.3 |
| Average score: Claws 12 w. | 4.7 | 3.3 | 2.1 |

REFERENCES (1) Metchnikoff, E. 1908. Prolongation of Life. G.P. Putnam's Sons. New York.
(2) Shahani, K. M. and A. D. Ayebo. 1980. Role of dietary lactobacilli in gastrointestinal microecology. Am. J. Clin. Nutr. 33: 2448.
(3) Skrede, A., Ahlstrom, O. 2002. Bacterial Protein Produced on Natural Gas: A New Potential Feed Ingredient for Dogs Evaluated Using the Blue Fox as a Model. The American Society for Nutritional sciences J. Nutr. 132: 1668S-1669.
(4) Savage, D. C. 1991. Gastrointestinal Microbial Ecology; possible Modes of Action of Direct-fed Microbials in Animal Production. In: Direct-fed Microbials in Animal Production; rh1; National Feed Ingredients Assoc.; Des Moines, Iowa; pp. 11-81.

(5) Savage, D. C. 1985. Effects on Host Animals of Bacteria Adhering to Epithelial Surfaces. In: Bacterial Adhesion, D. C. Savage and M. Fletcher (eds.); Plenum, N.Y.; pp. 437-463.

(6) Whitt, D. D. and D. C. Savage. 1981. Influence of indigenous microbiota on amount of protein and activities of alkaline phosphatase and disaccharidases in extracts of intestinal mucosa in mice. Appl. Environ. Micro. 42:513.

(7) Montes, A. J. and D. G. Pugh. 1993. The use of probiotics in food-animal practice. Vet. Med. March 1993:282.

(8) Klaenhammer, T. R. 1982. Microbiological considerations in selection and preparation of *Lactobacillus* strains for use as dietary adjuncts. J. Dairy Sci. 65: 1339.

(9). Baillon, M. L. A., Marshall-Jones, Z. V. & Butterwick, R. F. (2004) Effects of probiotic *Lactobacillus acidophilus* strain DSM13241 in healthy adult dogs. Am. J. Vet. Res. 65: 338-343.

(10). Tannock, G. W. (2002) Probiotics and Prebiotics: Where Are We Going? Caister Academic Press, Wymondham, UK.

(11) Ahlstrom, o., Skrede, A. 1998. Comparative Nutrient Digestibility in Dogs, Blue Foxes, Mink and Rats. The Journal of Nutrition Vol. 128 No. 12 December 1998, pp 2676S-2677S.

(12) Hansen, N. E., Finne, L., Skrede, A. & Tauson, A.-H. 1991. Energiforsyningen hos mink og raev. NJF-utredning:rapport no. 63, DSR forlag, Den Kgl. Veterinaer-og Landbohøjskole, Copenhagen, 59 pp. (In Danish.)

(13) Roth, F. X., Gruber, K. and Kirchgessner, M. 2001. The ideal dietary amino acid pattern for broilerchicks of age 7 to 28 days. Arch. Geflügelk. 65: 199-206.

(14) Boisen, S., Hvelplund, T. and Weisbjerg, M. R. 2000. Ideal amino acid profiles as a basis for feed protein evaluation. Livest. Prod. Sci. 64: 239-251.

(15) Børsting, C. F. and Clausen, T. N. 1996. Requirements of essential amino acids for mink in the growing-furring period. Proc. VIth Int. Sci. Congr. Fur Anim. Prod. Applied Science Reports 28: 15-24. Polish Society of Animal Production, Warsaw.

(16) Skrede, A. 1978. Utilization of fish and animal byproducts in mink nutrition. I. Effect of source and level of protein on nitrogen balance, postweaning growth and characteristics of winter fur quality. Acta Agric. Scand. 28: 105-129.

(17) Glem-Hansen, N. 1980. The protein requirements of mink during the growth period. Acta Agric. Scand. 30, 336-344.

(18) Glem-Hansen, N. 1982. Utilization of L-cystine and L- and D-methionine by mink during the period of intensive hair growth. Acta Agric. Scand. 32, 167-170.

(19) Dahlman, T., Niemelä, P., Kiiskinen, T., Mäkelä, J. and Korhonen, H. 1996. Influence of protein quantity and quality on mink. Proc. VIth Int. Sci. Congr. Fur Anim. Prod. Applied Science Reports 28: 9-14. Polish Society of Animal Production, Warsaw.

(20 Damgaard, B. 1997. Dietary protein supply to mink (Mustela vison)—Effects on physiological parameters, growth performance and health. Ph. D. Thesis. Department of Animal Science and Animal Health, the Royal Veterinary and Agricultural University, Frederiksberg C, Denmark. 31 pp.

(21) Kerminen-Hakkio, M., Dahlman, T., Niemelä, P., Jalava, T., Rekilä, T. and Syrjälä-Qvist, L. 2000. Effect of dietary protein level and quality on growth rate and fur parameters in mink. Proc. VIIth Int. Sci. Congr. Fur Anim. Prod. Scientifur 24: 7-12, Kastoria, Greece.

(22) Hidalgo, I. J., Raub, T. J., Borchardt, R. T. 1989. Characterisation of the human colonic carcinoma cell line (Caco-2) as a model system for intestinal epithelial permeability. Gastroenterology 96:736-749

(23) Thwaites, D. T., Brown, C. D. A., Hirst, B. H. Simmons, N. L. 1993a. Transepithelial glycylsarcosine transport in intestinal Caco-2 cells mediated by expression of H+-coupled carriers at both apical and basal membranes. J. Biol. Chem. 268:7640-7642

(24) Thwaites, D. T., Hirst, B. H., Simmons, N. L. 1994a. Substrate specificity of the di/tripeptide transporter in human intestinal epithelia (Caco-2): identification of substrates that undergo H+-coupled absorption. Br. J. Pharmacol. 113: 1050-1056

(25) Thwaites, D. T., McEwan, G. T. A., Brown, C. D. A., Hirst, B. H., Simmons, N. L. 1993b. Na+-independent, H+-coupled transepithelial b-alanine absorption by human intestinal Caco-2 cell monolayers. J. Biol. Chem. 268: 18438-18441

(26) Thwaites, D. T., McEwan, G. T. A., Brown, C. D. A., Hirst, B. H., Simmons, N. L. 1994b. L-Alanine absorption in human intestinal cells driven by the proton electrochemical gradient. J. Membrane Biol. 140:143-151

(27) Thwaites, D. T., Cavet, M., Hirst, B. H., Simmons, N. L. 1995. Angiotension-converting enzyme (ACE) inhibitor transport in human intestinal epithelial (Caco-2) cells. Br. J. Pharmacol 114:981-986

(28) Thwaites D. T., Markovich D. Murer H. Simmons N. L. 1996. Na+-independent Lysine Transport in Human Intestinal Caco-2 Cells. Journal of Membrane Biology. 151: 215-224.

What is claimed is:

1. A biologically pure culture of *Lactobacillus reuteri* strain ATCC PTA-6127.

2. A product for improving fur and claw quality in pet-animals comprising:
   a) a biologically pure culture of a strain of *Lactobacillus reuteri* ATCC PTA-6127; and
   b) a feed mixture wherein the feed mixture is coated with a coating substrate, and then with a dry spray of the biologically pure culture of the strain of *Lactobacillus reuteri*.

3. The product of claim 2, wherein the feed mixture is pelleted.

4. The product of claim 2, wherein the feed mixture comprises corn, corn gluten, chicken and fish meal, salts, vitamins and minerals.

5. The product of claim 2, wherein the coating substrate comprises tallow fat.

6. The product of claim 5, wherein the biologically pure culture is applied by dry spraying at a level of $10^7$ CFU/gram of product, before the tallow sets so as to adhere to or be partially penetrated in the fat layer.

7. The product of claim 2, wherein the product is in the form selected from the group consisting of feed, tablets, and capsules.

8. A feed product for improving fur and claw quality in pet-animals comprising a biologically pure culture of *Lactobacillus reuteri* ATCC PTA-6127.

9. A method of improving fur and claw quality in a pet-animal comprising providing a product according to claim 2 to the pet-animal.

* * * * *